United States Patent
Huang et al.

(10) Patent No.: US 9,121,799 B2
(45) Date of Patent: Sep. 1, 2015

(54) MULTI-AXLE JOINT SHIFTING LOADING APPARATUS FOR PROCESSING CENTER AND DETECTION METHOD FOR STATIC STIFFNESS DISTRIBUTION

(75) Inventors: Yumei Huang, Xi'an (CN); Xingang Yang, Xi'an (CN); Ye Hui, Xi'an (CN); Rui Zhao, Xi'an (CN)

(73) Assignee: XI'AN UNIVERSITY OF TECHNOLOGY, Xi'an (CN)

( * ) Notice: Subject to any disclaimer, the term of this patent is extended or adjusted under 35 U.S.C. 154(b) by 381 days.

(21) Appl. No.: 13/811,257

(22) PCT Filed: Aug. 4, 2011

(86) PCT No.: PCT/CN2011/078005
§ 371 (c)(1),
(2), (4) Date: Jan. 18, 2013

(87) PCT Pub. No.: WO2012/016534
PCT Pub. Date: Feb. 9, 2012

(65) Prior Publication Data
US 2013/0111981 A1    May 9, 2013

(30) Foreign Application Priority Data
Aug. 6, 2010  (CN) .......................... 2010 1 0246643

(51) Int. Cl.
*G01N 3/40*     (2006.01)
*G01M 99/00*   (2011.01)
*B23Q 17/00*   (2006.01)

(52) U.S. Cl.
CPC ................. *G01N 3/40* (2013.01); *B23Q 17/00* (2013.01); *G01M 99/007* (2013.01); *B23Q 2230/002* (2013.01)

(58) Field of Classification Search
None
See application file for complete search history.

(56) References Cited

U.S. PATENT DOCUMENTS 4,559,600 A * 12/1985 Rao ............................... 700/175
6,145,370 A * 11/2000 Evans ................................ 73/7
6,526,837 B1   3/2003 Grote et al.

(Continued)

FOREIGN PATENT DOCUMENTS

CN           1161267 A        10/1997
CN         101000283 A         7/2007

(Continued)

OTHER PUBLICATIONS

Ma, Zaixi et al., "A New Machine Tool Static Stiffness Measuring System," Machine Tool, 7th Edition, Apr. 16, 1991, pp. 40-41, China.

*Primary Examiner* — Andre Allen
(74) *Attorney, Agent, or Firm* — Novick, Kim & Lee, PLLC; Sang Ho Lee

(57) ABSTRACT

Disclosed is an operating position changeable loading apparatus with multi-axis joint movement used on machining center. The apparatus consists of a load-receiving test piece and a load-exerting component. Moving the load-exerting component and the load-receiving test piece to a preset loading position according to a multi-axis joint movement, with the displacement value measured by displacement sensors and the amount of simulated load measured by a force sensor of the loaded-exerting component, a stiffness of the load-exertion position under a simulated load can be derived. Changing the load-exertion position, repeating in sequence the previous steps, a stiffness distribution under the simulated load can be derived.

7 Claims, 3 Drawing Sheets

(56) References Cited

U.S. PATENT DOCUMENTS

| | | | |
|---|---|---|---|
| 2003/0009898 A1* | 1/2003 | Slocum et al. | 33/706 |
| 2005/0081360 A1 | 4/2005 | Blocher et al. | |
| 2007/0261502 A1* | 11/2007 | Steinkamp et al. | 73/862.046 |
| 2009/0087253 A1* | 4/2009 | Spratte et al. | 403/131 |
| 2009/0136288 A1* | 5/2009 | Ersoy et al. | 403/76 |
| 2013/0180350 A1* | 7/2013 | Kraus et al. | 74/108 |
| 2015/0128716 A1* | 5/2015 | Mizuta et al. | 73/790 |

FOREIGN PATENT DOCUMENTS

| | | |
|---|---|---|
| CN | 101029856 A | 9/2007 |
| CN | 201037803 Y | 3/2008 |
| CN | 101193727 A | 6/2008 |
| CN | 101480782 A | 7/2009 |
| CN | 101852671 A | 10/2010 |
| CN | 101915679 A | 12/2010 |
| CN | 101941102 A | 1/2011 |
| JP | 2000202737 A | 7/2006 |
| KR | 100786526 B1 | 12/2007 |
| SU | 1206010 A1 | 1/1986 |
| SU | 1335400 A1 | 9/1987 |
| WO | 2009015789 A1 | 2/2009 |
| WO | WO 2012025065 A1 * | 3/2012 |

\* cited by examiner

MULTI-AXLE JOINT SHIFTING LOADING APPARATUS FOR PROCESSING CENTER AND DETECTION METHOD FOR STATIC STIFFNESS DISTRIBUTION

TECHNICAL FIELD

The present invention belongs to a detection technology for simulating static stiffness of numerical controlling machine tools under loads at different positions in a working space, and more particularly relates to a multi-axle joint shifting loading apparatus for a processing center and a detection method for a static stiffness distribution.

BACKGROUND ART

In a working space of a machine tool, the magnitude of loads (including force and moment) and loading positions of members of the machine tool vary as the position of the machining point varies, so that a static stiffness distribution of the machine tool changes. The change in static stiffness at different machining positions may be described by a stiffness distribution. The magnitude of the static stiffness and the static stiffness distribution influence the machining precision directly (especially the stiffness distribution influences the shape precision of the machining surface directly), and influence the vibration characteristics of the machine tool at the same time.

In a design stage, the static stiffness and the static stiffness distribution of a design scheme may be predicted using an analysis method, and then the design scheme is revised according to the predicted results so that the stiffness and the stiffness distribution are improved.

One of the purposes of the static stiffness detection test for the numerical control machine tool is to provide data for evaluating the static stiffness of the machine tool, and the another one is to check and verify the correctness of the predicting method for the static stiffness and static stiffness distribution and the scheme revising method, so as to provide experimental means for researching and improving the prediction and the scheme revising method.

Regarding multi-axle joint numerical machine tools, various numerical machine tools have different principles for forming machining surface and different movement functions of servo axles of their feeding system, as well as different joint relations and numbers of joint axles for maintaining a strict movement relationship among numerical axles; loads carried by various multi-axle joint numerical machine tools have different properties, and various multi-axle joint numerical machine tools have different load changing rules at various machining positions, and different ratios among loads in respective directions. Therefore, loads simulation apparatuses and their corresponding detecting methods are different from one another for various multi-axle joint numerical control machine tools. For example, a 5-axle processing center having three linear movements in Z axle, Y axle and X axle, and two rotation movements around C axle and A axle, may machine various kinds of complex surfaces by the joint movement of the Z axle, Y axle, X axle C axle and A axle. In the actual machining, forces in three directions are applied to a machining point, and a load from a worktable is transmitted through the workpiece, and the worktable will carry six cutting loads (three forces Fx, Fy and Fz and three moments Mx, My and Mz); meanwhile, the main axle will also carry six cutting loads.

In a machine tool static stiffness test, cutting loads are replaced by simulation loads. The processing center static stiffness detection apparatus and the detecting method available both in China and abroad can only detect the static stiffness at one determined position, and cannot detect the static stiffness distribution. The 5-axle processing center may machine various kinds of complex surfaces through a joint movement of the Z axle, Y axle, X axle C axle and A axle, the position of a point to be machined varies during machining, and accordingly the positions of the members on Z axle, Y axle, X axle C axle and A axle vary, so that both the static stiffness at the main axle side and that at the worktable side change as the position of a machined point on a workpiece varies. The change in stiffness influences the shape precision of a machining surface directly, and thus it is necessary to detect the static stiffness distribution of a processing center.

The processing center static stiffness detection apparatuses and detecting methods both in China and abroad cannot apply six simulation loads to the main axle. Therefore the cutting load cannot be fully simulated at the main axle side. The worktable and the main axle carry a load and an anti-load, respectively, so that the cutting load at the worktable side cannot be fully simulated, though six simulation loads can be applied at this side. In the machine tool static stiffness test, the cutting loads are replaced by the simulation loads, simulation forces in three directions are applied to a loading point, and it is desired that both the main axle side and the worktable side of the processing center can endure six simulation loads for fully simulating six simulation loads of the cutting loads.

DISCLOSURE OF INVENTION

Technical Problems

One object of the present invention is to provide a multi-axle joint shifting loading apparatus for a processing center to solve the technical problem that the existing processing center static stiffness detection apparatuses can only detect the static stiffness at one determined point, but cannot detect the static stiffness distribution, nor can they fully simulate the cutting loads.

The other object of the present invention is to provide a method for detecting the static stiffness distribution using the above multi-axle joint shifting loading apparatus.

Technical Solution

The technical solution adopted by the present invention is a multi-axle joint shifting loading apparatus for a processing center which includes a load-receiving test piece and a load-exerting component for simulating loading; the load-receiving test piece is provided with a load-receiving surface thereon; the load-exerting component includes a steel ball, a cap, a ball socket, a bent board, a force sensor and a connection component A; one end of the ball socket is fixedly connected with the cap, the steel ball is embedded in the cap and the ball socket, and a part of the steel ball is at the outside of the cap; and the other end of the ball socket is fixedly connected with one end of the bent board, the other end of the bent board is fixedly connected with one end of the force sensor, and the other end of the force sensor is fixedly connected with the connection component A.

Wherein, the connection component A is further provided with a connection component B; the connection component A has a cylindrical shape, the connection component B is composed of a left connection member and a right connection member; each of the left connection member and the right connection member includes a horizontal bar disposed horizontally and a vertical bar disposed on the horizontal bar and being perpendicular to the horizontal bar; both the left connection member and the right connection member are fixed on the connection component A, and are formed as a symmetrical structure with a central line of the connection component A as a symmetry line.

In addition, the load-receiving surface of the load-receiving test piece is in any shape.

Furthermore, the multi-axle joint shifting loading apparatus is used for various kinds of a turning-milling composite processing center, an upright processing center or a horizontal processing center.

Another technical solution adopted by the present invention is: when the shifting loading apparatus is used for a turning-milling composite processing center to detect the static stiffness distribution, the shifting loading apparatus is configured as follows: the apparatus includes a load-receiving test piece and a load-exerting component for simulating loading; the load-receiving test piece is provided with a load-receiving surface thereon; the load-exerting component includes a steel ball, a cap, a ball socket, a bent board, a force sensor and a connection component A; one end of the ball socket is fixedly connected with the cap, the steel ball is embedded in the cap and the ball socket, and a part of the steel ball is at the outside of the cap; and the other end of the ball socket is fixedly connected with one end of the bent board, the other end of the bent board is fixedly connected with one end of the force sensor, and the other end of the force sensor is fixedly connected with the connection component A, wherein the steps for detecting static stiffness distribution using the apparatus are as follows:

firstly, the connection component A of the load-exerting component is fixedly connecting with the tool shank, wherein the tool shank is tensioned in a taper hole in an main axle, and the main axle is positioned; the load-receiving test piece is then mounted on a worktable; displacement sensors are mounted on the main axle, a main axle housing and the worktable, respectively; then the load-exerting component and the load-receiving test piece are moved to a preset first loading position through a joint movement of multiple axles and a normal of the load-receiving surface of the load-receiving test piece is disposed to be consistent with an axis L of the ball socket; the load-exerting component applies a simulation load to the load-receiving point on the load-receiving surface of the load-receiving test piece through fine adjustments to a joint movement of the multiple axles; stiffness under the simulated load at the loading position can be obtained from the displacement detected by the displacement sensors and the simulation load detected by the force sensor of the load-exerting component; then the load-exerting component and the load-receiving test piece are moved to a next loading position through the joint movement of the multiple axles and a normal of the load-receiving surface of the load-receiving test piece is adjusted to be consistent with the axis L of the ball socket, so that the stiffness at the next loading position is detected after changing the loading position through a multi-axle joint movement; and the above procedures are repeated so as to obtain the stiffness at different loading positions to obtain the stiffness distribution of the turning-milling composite processing center under the simulation load.

Another technical solution adopted by the present invention is: when the shifting loading apparatus is used for an upright processing center or a horizontal processing center to detect the static stiffness distribution, the shifting loading apparatus is configured as follows: the apparatus includes a load-receiving test piece and a load-exerting component for simulating loading; the load-receiving test piece is provided with a load-receiving surface thereon; the load-exerting component includes a steel ball, a cap, a ball socket, a bent board, a force sensor and a connection component A; one end of the ball socket is fixedly connected with the cap, the steel ball is embedded in the cap and the ball socket, and a part of the steel ball is at the outside of the cap; and the other end of the ball socket is fixedly connected with one end of the bent board, the other end of the bent board is fixedly connected with one end of the force sensor, and the other end of the force sensor is fixedly connected with the connection component A; the connection component A is further provided with a connection component B; the connection component A has a cylindrical shape, the connection component B is composed of a left connection member and a right connection member; each of the left connection member and the right connection member includes a horizontal bar disposed horizontally and a vertical bar disposed on the horizontal bar and being perpendicular to the horizontal bar; both the left connection member and the right connection member are fixed on the connection component A, and are formed as a symmetrical structure with a central line of the connection component A as a symmetry line, wherein the steps for detecting static stiffness distribution using the apparatus are as follows:

firstly, the connection component A of the load-exerting component is fixedly connecting with the tool shank, wherein the tool shank is tensioned in a taper hole in an main axle, and the connection component B disposed on the connection component A is connected with the a main axle housing through the vertical bar; the load-receiving test piece is then mounted on a worktable; displacement sensors are mounted on the main axle, the main axle housing and the worktable, respectively; then the load-exerting component and the load-receiving test piece are moved to a preset first loading position through a joint movement of multiple axles and a normal of the load-receiving surface of the load-receiving test piece is disposed to be consistent with an axis L of the ball socket; the load-exerting component applies a simulation load to the load-receiving point on the load-receiving surface of the load-receiving test piece through fine adjustments to a joint movement of the multiple axles; stiffness under the simulated load at the loading position can be obtained from the displacement detected by the displacement sensors and the simulation load detected by the force sensor of the load-exerting component; then the load-exerting component and the load-receiving test piece are moved to a next loading position through the joint movement of the multiple axles and a normal of the load-receiving surface of the load-receiving test piece is adjusted to be consistent with the axis L of the ball socket, so that the stiffness at the next loading position is detected after changing the loading position through a multi-axle joint movement; and the above procedures are repeated so as to obtain the stiffness at different loading positions to obtain the stiffness distribution of the upright processing center or the horizontal processing center under the simulation load.

Advantageous Effect

The advantageous effects of the present invention are: full loads (including force and moment) for simulation can be applied; the static stiffness distribution of a processing center can be detected by changing the loading position through a multi-axle joint movement; and various processing surface shapes of load-receiving test can be designed by designing and adjusting/changing the direction of ball socket axis of the load-exerting component, so that experimental requirements can be satisfied for different ratios of simulation loads and different number of joint axles (varying from 3 axles to 5 axles).

DETAILED DESCRIPTION OF THE PREFERRED EMBODIMENT

Reference will now be made in detail to the embodiments of the present invention, taken in conjunction with the accompanying drawings and the detailed embodiments.

Figure 1:
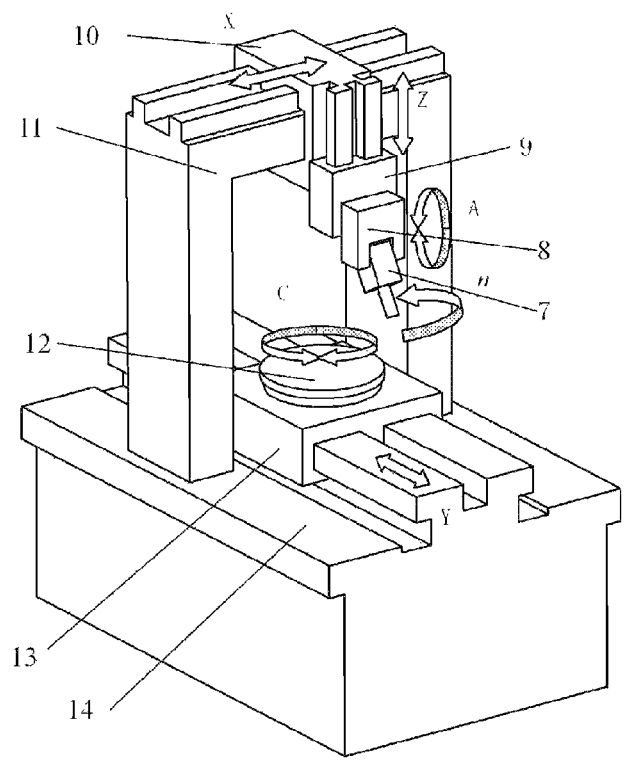
FIG. 1 is a schematic view of movement functions of a typical 5-axle joint processing center.
Figure 2:
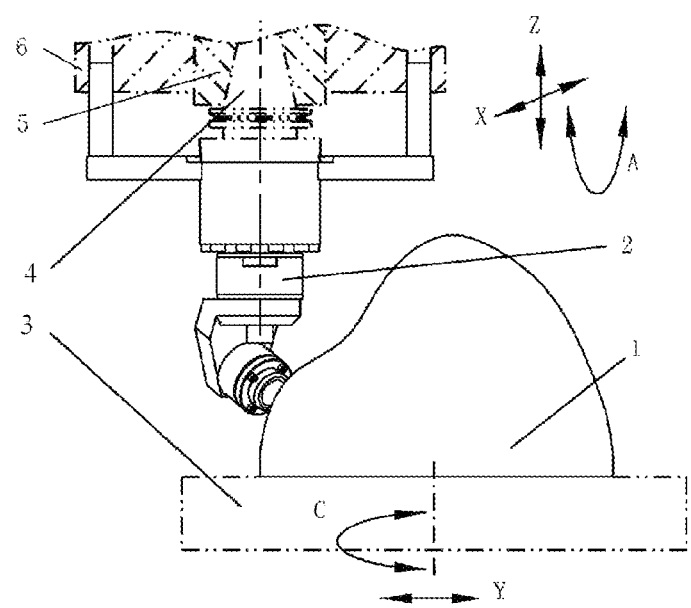
FIG. 2 is a schematic view of a multi-axle joint shifting loading apparatus and installation and connection thereof according to the present invention.

FIG. 1 shows a 5-axle processing center having three linear movements in Z axle, Y axle and X axle and two slewing movements about C axle and A axle, wherein the 5-axle processing center is mainly composed of a main axle part 7, an A axle part 8, a Z axle part 9, a X axle part 0, a pillar beam part 11, a C axle part 12, a Y axle part 13, a machine body part 14 and a worktable 3; n indicates the main axle slewing movement which is a cutting movement and does not join in the movement joint; the main axle 5 and the worktable 3 operate as end executors for carrying objects; the main axle part 7 includes a tool shank 4, a main axle 5 and a main axle housing 6 (as shown in FIG. 2); the tool shank 4 side implements A axle movement, Z movement and X axle movement, the workpiece is mounted on the worktable 3 and the workpiece side implements Y axle movement and C axle movement.

Figure 3:
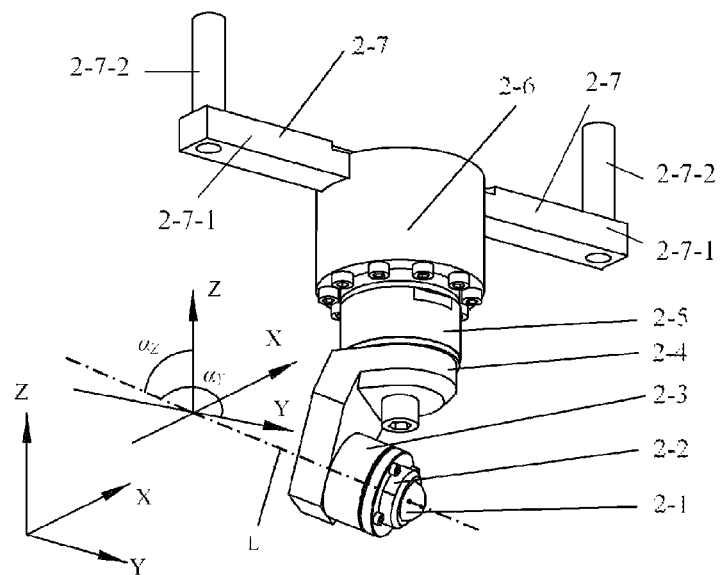
FIG. 3 is a structural schematic view of a load-exerting component of the multi-axle joint shifting loading apparatus according to the present invention.
Figure 4:
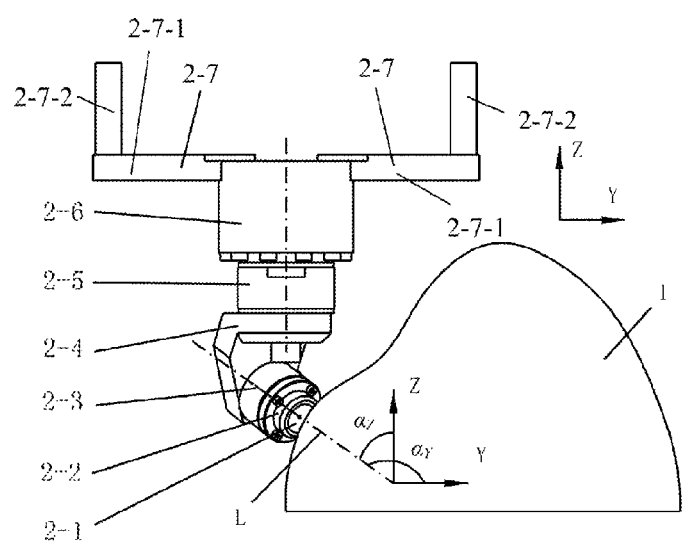
FIG. 4 is a structural schematic view of the multi-axle joint shifting loading apparatus according to a first embodiment of the present invention.
Figure 5:
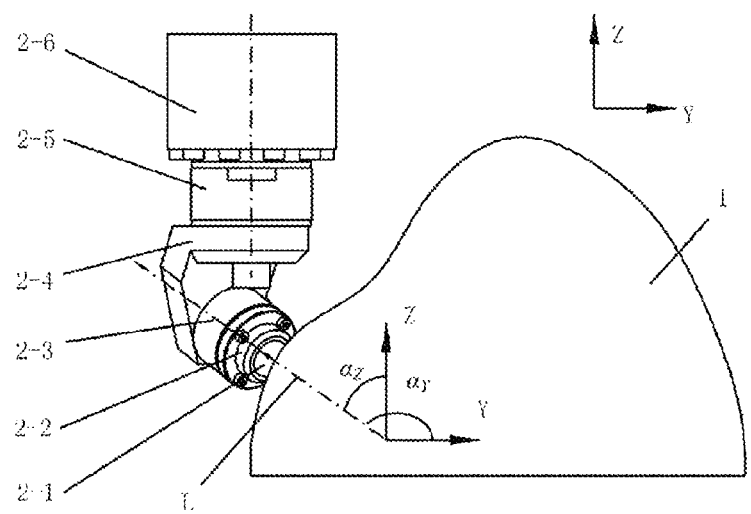
FIG. 5 is a structural schematic view of the multi-axle joint shifting loading apparatus according to a second embodiment of the present invention, wherein, the reference numbers are as follows: 1, load-receiving test piece; 2, load-exerting component; 3, worktable; 4, tool shank; 5, main axle; 6, main axle housing; 2-1, steel ball; 2-2, cap; 2-3, ball socket; 2-4, bent board; 2-5, force sensor; 2-6 connection component A; 2-7, connection component B; 2-7-1, horizontal bar; 2-7-2, vertical bar; 7, main axle part; 8, A axle part; 9, Z axle part; 10, X axle part; 11, pillar beam part; 12, C axle part; 13, Y axle part; 14, machine body part; L, axis of ball socket.

As shown in FIG. 2, the present invention provides a processing center multi-axle joint shifting loading apparatus, which includes a load-receiving test piece and a load-exerting component 2 for simulating loading; the load-receiving test piece is provided with a load-receiving surface which may be designed to be any kind of shapes; as shown in FIGS. 3-5, the load-exerting component 2 includes a steel ball 2-1, a cap 2-2, a ball socket 2-3, a bent board 2-4, a force sensor 2-5 and a connection component A 2-6; one end of the ball socket 3 is fixedly connected with the cap 2-2, the steel ball is embedded in the cap 2-2 and the ball socket 2-3, while a part of the steel ball is at the outside of the cap 2-2; and the other end of the ball socket 2-3 is fixedly connected with one end of the bent board 2-4, the other end of the bent board 2-4 is fixedly connected with one end of the force sensor 2-5, while the other end of the force sensor 2-5 is fixedly connected with the connection component A 2-6. When the shifting loading apparatus according to the present invention is employed in a turning-milling composite processing center, the connection component A 2-6 is fixedly connected with the tool shank 2-4 which is tensioned in a taper hole in the main axle 5. Once the main axle is positioned to mount the load-receiving test piece 1 on the worktable 3, the detection for the static stiffness distribution of the processing center can be performed. When the detection loading apparatus according to the present invention is employed in various upright processing centers and horizontal processing centers, based on the shifting loading apparatus shown in FIG. 5, a connection component B 2-7 is further disposed on the connection component A 2-6, and it is shown in FIGS. 3 and 4 that the connection component A 2-6 has a cylindrical shape and the connection component B 2-7 is composed of a left connection member and a right connection member; each of the left connection member and the right connection member is composed of a horizontal bar 2-7-1 disposed horizontally and a vertical bar 2-7-2 disposed on the horizontal bar 2-7-1 and being perpendicular to the horizontal bar 2-7-1; both the left connection member and the right connection member are fixed on the connection component A 2-6 through the horizontal bar 2-7-1, and are formed as a symmetrical structure with a central line of the connection component A 2-6 as a symmetry line. The connection component A 2-6 and the tool shank 4 are fixedly connected, the tool shank 4 is tensioned in a taper hole in the main axle 5, and the connection component B 2-7 disposed on the connection component A 2-6 is connected with the main axle housing 6 through the vertical bar 2-7-2, and once the load-receiving test piece is mounted on the worktable 3, the detection for the static stiffness distribution of the processing center can be performed.

As shown in FIGS. 3, 4 and 5, according to a ratio of the simulation load, the axis L is designed to form angles $\alpha_y$ and $\alpha_z$ relative to Y axle and Z axle, respectively, the steel ball 2-1 is in point contact with the load-receiving surface of the load-receiving test piece where the simulation load may be decomposed into three component forces Fx, Fy and Fz, the ratios among the forces Fx, Fy and Fz will vary when the angles $\alpha_y$ and $\alpha_z$ vary, and the moments Mx, My and Mz which are equivalent moments from the forces Fx, Fy and Fz at the worktable and the main axle change as well.

Embodiment 1

When the shifting loading apparatus according to the present invention is used in a 5-axle joint upright processing center or a horizontal processing center, the method for detecting the processing center static stiffness distribution is as follows: as shown in FIGS. 2 and 4, firstly the connection component A 2-6 of the load-exerting component 2 is fixedly connecting with the tool shank 4, wherein the tool shank 4 is tensioned in the taper hole in the main axle 5, and the connection component B 2-7 disposed on the connection component A 2-6 is connected with the main axle housing 6 through the vertical bar 2-7-2; the load-receiving test piece 1 is mounted on the worktable 3; a displacement sensor is mounted, which may be installed in plural, for example, on the main axle 5, the main axle housing 6 and the worktable 3; then the load-exerting component 2 and the load-receiving test piece 1 are moved to a preset first loading position through a joint movement of Z axle, Y axle, X axle, C axle and A axle and a normal on the load-receiving point of the load-receiving surface of the load-receiving test piece 1 is adjusted to be consistent with the axis L of the ball socket; the load-exerting component 2 applies a simulation load to the load-receiving point on the load-receiving surface of the load-receiving test piece through fine adjustments to a joint movement of the Z axle, Y axle, X axle, C axle and A axle; stiffness under the simulated load at the loading position can be obtained from the displacement detected by the displacement sensor and the simulation load detected by the force sensor 5 of the load-exerting component 2; then the load-exerting component 2 and the load-receiving test piece are moved to a next loading position through the joint movement of Z axle, Y axle, X axle, C axle and A axle again, and a normal of the load-receiving surface of the load-receiving test piece is adjusted to be consistent with the axis L of the ball socket 3, that is to say, the stiffness at the next loading position is detected after changing the loading position through a 5-axle joint; and the above procedures are repeated and then the stiffness distribution under the simulation load can be obtained.

Embodiment 2

When the shifting loading apparatus according to the present invention is used in a 5-axle joint turning-milling composite processing center, the method differs from the first embodiment in that a position function is utilized when the main axle performs a turning cutting, and thus the connection component B 2-7 is not required, wherein the multi-axle joint shifting loading apparatus is illustrated in FIG. 5, as long as the connection component A 2-6 and the tool shank 4 are fixedly connected, the tool shank 4 is tensioned in a taper hole in the main axle 5, and the load-receiving test piece 1 is mounted on the worktable 3, the detection method can be performed. In this case, the method for detecting the static stiffness distribution of the processing center is the same as that of the first embodiment, that is to say, the method also change the loading position through a joint movement of Z axle, Y axle, X axle, C axle and A axle, the detailed description of which is omitted herein.

Embodiment 3

When the shifting loading apparatus according to the present invention is used in a 4-axle joint processing center having X axle, Y axle, Z axle and C axle (that is, the processing center shown in FIG. 1 has no A axle), the load exerting component 2 is connected to the processing center in the same manner of the first embodiment with a difference that the loading position is changed through a joint movement of X axle, Y axle, Z axle and C axle. The shape of the load-receiving surface of the load-receiving test piece 1 can be designed in a rather simple manner.

Among the axles, a slewing axle, an axis of which is parallel with X axle is called as A axle; and a slewing axle, an axis of which is parallel with Y axle is called as B axle, and a slewing axle, an axis of which is parallel with Z axle is called as C axle.

The invention claimed is:

1. A multi-axle joint shifting loading apparatus for a processing center, being characterized in: the apparatus comprises a load-receiving test piece (1) and a load-exerting component (2) for simulating loading; the load-receiving test piece (1) is provided with a load-receiving surface thereon; the load-exerting component (2) comprises a steel ball (2-1), a cap (2-2), a ball socket (2-3), a bent board (2-4), a force sensor (2-5) and a connection component A (2-6); one end of the ball socket (2-3) is fixedly connected with the cap (2-2), the steel ball (2-1) is embedded in the cap (2-2) and the ball socket (2-3), and a part of the steel ball (2-1) is at the outside of the cap (2-2); and the other end of the ball socket (2-3) is fixedly connected with one end of the bent board (2-4), the other end of the bent board (2-4) is fixedly connected with one end of the force sensor (2-5), and the other end of the force sensor (2-5) is fixedly connected with the connection component A (2-6).

2. The apparatus according to claim 1, being characterized in: the connection component A (2-6) is further provided with a connection component B (2-7); the connection component A (2-6) has a cylindrical shape, the connection component B (2-7) is composed of a left connection member and a right connection member; each of the left connection member and the right connection member comprises a horizontal bar (2-7-1) disposed horizontally and a vertical bar (2-7-2) disposed on the horizontal bar (2-7-1) and being perpendicular to the horizontal bar (2-7-1); both the left connection member and the right connection member are fixed on the connection component A (2-6), and are formed as a symmetrical structure with a central line of the connection component A (2-6) as a symmetry line.

3. The apparatus according to claim 1, being characterized in that the load-receiving surface of the load-receiving test piece (1) is in any shape.

4. The apparatus according to claim 1, being characterized in that the multi-axle joint shifting loading apparatus is used for a turning-milling composite processing center.

5. The apparatus according to claim 2, being characterized in that the multi-axle joint shifting loading apparatus is used for an upright processing center or a horizontal processing center.

6. A method for detecting static stiffness distribution using a multi-axle joint shifting loading apparatus, being characterized in that when the shifting loading apparatus is used for a turning-milling composite processing center to detect the static stiffness distribution, the shifting loading apparatus is configured as follows: the apparatus comprises a load-receiving test piece (1) and a load-exerting component (2) for simulating loading; the load-receiving test piece (1) is provided with a load-receiving surface thereon; the load-exerting component (2) comprises a steel ball (2-1), a cap (2-2), a ball socket (2-3), a bent board (2-4), a force sensor (2-5) and a connection component A (2-6); one end of the ball socket (2-3) is fixedly connected with the cap (2-2), the steel ball (2-1) is embedded in the cap (2-2) and the ball socket (2-3), and a part of the steel ball (2-1) is at the outside of the cap (2-2); and the other end of the ball socket (2-3) is fixedly connected with one end of the bent board (2-4), the other end of the bent board (2-4) is fixedly connected with one end of the force sensor (2-5), and the other end of the force sensor (2-5) is fixedly connected with the connection component A (2-6), wherein the method for detecting static stiffness distribution using the apparatus comprises steps as follows:

firstly, the connection component A (2-6) of the load-exerting component (2) is fixedly connecting with the tool shank (2-4), wherein the tool shank (4) is tensioned in a taper hole in an main axle (5), and the main axle is positioned; the load-receiving test piece (1) is then mounted on a worktable (3); displacement sensors are mounted on the main axle (5), a main axle housing (6) and the worktable (3), respectively; then the load-exerting component (2) and the load-receiving test piece (1) are moved to a preset first loading position through a joint movement of multiple axles and a normal of the load-receiving surface of the load-receiving test piece is disposed to be consistent with an axis L of the ball socket (2-3); the load-exerting component 2 applies a simulation load to the load-receiving point on the load-receiving surface of the load-receiving test piece (1) through fine adjustments to a joint movement of the multiple axles; stiffness under the simulated load at the loading position can be obtained from the displacement detected by the displacement sensors and the simulation load detected by the force sensor (2-5) of the load-exerting component (2); then the load-exerting component (2) and the load-receiving test piece (1) are moved to a next loading position through the joint movement of the multiple axles and a normal of the load-receiving surface of the load-receiving test piece is adjusted to be consistent with the axis L of the ball socket (2-3), so that the stiffness at the next loading position is detected after changing the loading position through a multi-axle joint movement; and the above procedures are repeated so as to obtain the stiffness at different loading positions to obtain the stiffness distribution of the turning-milling composite processing center under the simulation load.

7. A method for detecting static stiffness distribution using a multi-axle joint shifting loading apparatus, being characterized in that when the shifting loading apparatus is used for an upright processing center or a horizontal processing center to detect the static stiffness distribution, the shifting loading apparatus is configured as follows: the apparatus comprises a load-receiving test piece (1) and a load-exerting component (2) for simulating loading; the load-receiving test piece (1) is provided with a load-receiving surface thereon; the load-exerting component (2) comprises a steel ball (2-1), a cap (2-2), a ball socket (2-3), a bent board (2-4), a force sensor (2-5) and a connection component A (2-6); one end of the ball socket (2-3) is fixedly connected with the cap (2-2), the steel ball (2-1) is embedded in the cap (2-2) and the ball socket (2-3), and a part of the steel ball (2-1) is at the outside of the cap (2-2); and the other end of the ball socket (2-3) is fixedly connected with one end of the bent board (2-4), the other end of the bent board (2-4) is fixedly connected with one end of the force sensor (2-5), and the other end of the force sensor (2-5) is fixedly connected with the connection component A (2-6); the connection component A (2-6) is further provided with a connection component B (2-7); the connection component A (2-6) has a cylindrical shape, the connection component B (2-7) is composed of a left connection member and a right connection member; each of the left connection member and the right connection member comprises a horizontal bar (2-7-1) disposed horizontally and a vertical bar (2-7-2) disposed on the horizontal bar (2-7-1) and being perpendicular to the horizontal bar (2-7-1); both the left connection member and the right connection member are fixed on the connection component A (2-6), and are formed as a symmetrical structure with a central line of the connection component A (2-6) as a symmetry line, wherein the method for detecting static stiffness distribution using the apparatus comprises steps as follows:

firstly, the connection component A (2-6) of the load-exerting component (2) is fixedly connecting with the tool shank (2-4), wherein the tool shank (4) is tensioned in a taper hole in an main axle (5), and the connection component B (2-7) disposed on the connection component A (2-6) is connected with the a main axle housing (6) through the vertical bar (2-7-2); the load-receiving test piece (1) is then mounted on a worktable (3); displacement sensors are mounted on the main axle (5), the main axle housing (6) and the worktable (3), respectively; then the load-exerting component (2) and the load-receiving test piece (1) are moved to a preset first loading position through a joint movement of multiple axles and a normal of the load-receiving surface of the load-receiving test piece is adjusted to be consistent with an axis L of the ball socket (2-3); the load-exerting component 2 applies a simulation load to the load-receiving point on the load-receiving surface of the load-receiving test piece (1) through fine adjustments to a joint movement of the multiple axles; stiffness under the simulated load at the loading position can be obtained from the displacement detected by the displacement sensors and the simulation load detected by the force sensor (2-5) of the load-exerting component (2); then the load-exerting component (2) and the load-receiving test piece (1) are moved to a next loading position through the joint movement of the multiple axles and a normal of the load-receiving surface of the load-receiving test piece is adjusted to be consistent with the axis L of the ball socket (2-3), so that the stiffness at the next loading position is detected after changing the loading position through a multi-axle joint movement; and the above procedures are repeated so as to obtain the stiffness at different loading positions to obtain the stiffness distribution of the upright processing center or the horizontal processing center under the simulation load.

\* \* \* \* \*